United States Patent
Munderloh

(10) Patent No.: US 7,361,504 B2
(45) Date of Patent: Apr. 22, 2008

(54) **CULTURING *ANAPLASMA***

(75) Inventor: Ulrike G. Munderloh, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 199 days.

(21) Appl. No.: 10/524,338

(22) PCT Filed: Aug. 12, 2003

(86) PCT No.: PCT/US03/25208

§ 371 (c)(1),
(2), (4) Date: Aug. 1, 2005

(87) PCT Pub. No.: WO2004/016743

PCT Pub. Date: Feb. 26, 2004

(65) Prior Publication Data

US 2006/0057699 A1 Mar. 16, 2006

Related U.S. Application Data

(60) Provisional application No. 60/403,261, filed on Aug. 14, 2002.

(51) Int. Cl.
*C12N 5/00* (2006.01)
(52) U.S. Cl. ............................................. 435/325
(58) Field of Classification Search ................ 435/325
See application file for complete search history.

(56) References Cited

U.S. PATENT DOCUMENTS 3,616,202 A    10/1971  Marble
5,869,335 A    2/1999   Munderloh et al.
5,955,359 A    9/1999   Dumler et al.
5,976,860 A    11/1999  Coughlin et al.
5,989,848 A    11/1999  Dawson
6,284,238 B1   9/2001   Coughlin et al.

OTHER PUBLICATIONS

Blonin et al., "Persistence of tick-derived *Anaplasma marginale* in cultured bovine turbinate and endothelial cells," *Revue Élev. Méd. vét Pays trop.*, 1993, 46:49-56.

Kocan et al., "Immunization of cattle with *Anaplasma marginale* derived from tick cell culture," *Vet. Parasitol.*, 2001, 102:151-161.

Munderloh et al., "Isolation of the Equine Granulocytic Ehrlichiosis Agent, *Ehrlichia equi*, in Tick Cell Culture," *J. Clin. Microbiol.*, 1996, 34(3):664-670.

Munderloh et al., "Invasion and Intracellular Development of the Human Granulocytic Ehrlichiosis Agent in Tick Cell Culture," *J. Clin. Microbiol.*, 1999, 37(8):2518-2524.

Waghela et al., "In vitro cultivation of *Anaplasma marginale* in bovine erythrocytes co-cultured with endothelial cells," *Vet. Parasitol.*, 1997, 73:43-52.

Munderloh et al., "Establishment of the Tick (Acari: Ixodidae)-Borne Cattle Pathogen *Anaplasma Marginale* (Rickettsiales: Anaplasmataceae) In Tick Cell Culture," *J. Med. Entomol.*, 1996, 33(4):656-664.

Munderloh et al., "Infection of endothelial cells with *Anaplasma marginale* and *A. phagocytophilum*," *Vet. Microbiol.*, 2004, 101:53-64.

Mutunga et al., "Nitric Oxide is Produced by *Cowdria ruminanrium*-Infected Bovine Pulmonary Endothelial Cells In Vitro and Is Stimulated by Gamma Interferon," *Infection and Immunity*, 1998, 66(5):2115-2121.

*Primary Examiner*—Mark Navarro
(74) *Attorney, Agent, or Firm*—Fish & Richardson P.C.

(57) ABSTRACT

The invention provides mammalian cells stably infected with *Anaplasma* species, as well as materials and methods related to propagating *Anaplasma* species in mammalian cells and isolating such *Anaplasma* species from mammalian cells.

11 Claims, No Drawings

CULTURING *ANAPLASMA*

CROSS-REFERENCE TO RELATED APPLICATIONS

This application is a National Stage application under 35 U.S.C. §371 and claims benefit under 35 U.S.C. §119(a) of International Application No. PCT/US2003/025208 having an International Filing Date of Aug. 12, 2003, which claims the benefit of priority under 35 U.S.C. §119(e) of U.S. Application No. 60/403,261 having a filing date of Aug. 14, 2002.

BACKGROUND

1. Technical Field

The invention relates to methods and materials involved in culturing *Anaplasma* species.

2. Background Information

*Anaplasma phagocytophilum* and *Anaplasma marginale* are obligate intracellular, tick-borne rickettsial pathogens of humans and animals in North America, Europe, Australia, and Africa.

*A. phagocytophilum* (formerly known as "HGE agent," *Ehrlichia equi*, or *E. phagocytophila*) causes disease in humans, horses, small and large ruminants, dogs, and cats. *A. phagocytophilum* infections produce an acute, febrile illness accompanied by appearance of the microbes in white blood cells (specifically neutrophil granulocytes, as well as their precursors in the bone marrow), a reduction in the number of all blood cell types ("pancytopenia"), nausea, and confusion. Death occurs in about 5% of human patients if not treated promptly with tetracycline antibiotics. Diagnosis during the acute stage is difficult due to the absence of significant amounts of specific antibodies at that time, and a vaccine is not yet available. Recently, the causative agent has been isolated in cell lines of both human (the promyelocytic human leukemia cell line HL-60) and vector tick (the *Ixodes scapularis* cell lines ISE6 and IDE8) origin (See Munderloh et al., 1996, *J. Clin. Microbiol.*, 34:664-670; and Munderloh et al., 1999, *J. Clin. Microbiol.*, 37:2518-2524).

*A. marginale* is only known to infect red blood cells in ruminants, specifically cattle, often being referred to in the literature as an obligate intraerythrocytic pathogen. The disease is characterized by anemia, weakness, loss of milk production, retarded growth, abortion, and, in severe cases, death. The continuous propagation of this microbe in tick cell culture using the *I. scapularis* cell line IDE8 has been reported (Munderloh et al., 1996, *J. Med. Ent.*, 33:656-664). Despite their availability, tick cell-based cell culture systems have proven difficult to use for many research laboratories in industry and academia.

SUMMARY

The invention provides methods and materials related to propagating *Anaplasma* species in mammalian cells. Specifically, the invention provides for mammalian nucleated cells and mammalian adherent cells that are stably infected with an *Anaplasma* species, as well as methods and materials for making such mammalian cells. In addition, the invention provides methods and materials for (1) propagating various *Anaplasma* species in stably infected mammalian cells and (2) obtaining *Anaplasma* species from stably infected mammalian cells. The invention is based on the discovery that some mammalian cells such as endothelial cells and Vero cells can be stably infected with *Anaplasma* species, for example *A. marginale* and *A. phagocytophilum*. As such, these mammalian cells can be used as vehicles for propagating *Anaplasma* species in vitro. Such a culture system can allow *Anaplasma* to be clonally selected for genetic analysis, and can provide a ready source of *Anaplasma* that can be used as antigen for the production of anaplasmosis diagnostics and anaplasmosis treatment materials (e.g., *Anaplasma* vaccines).

In one aspect, the invention provides an isolated mammalian cell stably infected with an *Anaplasma* species such as *A. marginale, A. centrale, A. bovis, A. ovis*, and *A. platys*, wherein the mammalian cell is a nucleated cell. For example, the nucleated mammalian cell can be infected with *A. marginale*, or with *A. centrale*, or with *A. bovis*, or with *A. ovis*, or with *A. platys*.

In another aspect, the invention provides an isolated mammalian cell stably infected with an *Anaplasma* species such as *A. marginale, A. phagocytophilum, A. centrale, A. bovis, A. ovis*, and *A. platys*, wherein the mammalian cell is an adherent cell. For example, the adherent mammalian cell can be infected with *A. marginale*, or with *A. phagocytophilum*, or with *A. centrale*, or with *A. bovis*, or with *A. ovis*, or with *A. platys*.

Typically, the mammalian cell is an endothelial cell. Representative endothelial cells include, without limitation, a bovine corneal endothelial cell, a rhesus monkey microvascular endothelial cell, a human umbilical vascular endothelial cell, and a human microvascular endothelial cell.

In an embodiment, the invention provides an isolated mammalian cell stably infected with *Anaplasma marginale*, wherein the mammalian cell is a nucleated cell. In another embodiment, the invention provides an isolated mammalian cell stably infected with *Anaplasma phagocytophilum*, wherein the mammalian cell is an adherent cell.

In one aspect, the invention provides a method of making a mammalian cell that is stably infected with an *Anaplasma* species such as *A. marginale, A. centrale, A. bovis, A. ovis*, and *A. platys*. Such a method includes contacting a nucleated mammalian cell with the *Anaplasma* species to produce a mammalian cell stably infected with the *Anaplasma* species. For example, the nucleated mammalian cell can be contacted with *A. marginale*, or with *A. centrale*, or with *A. bovis*, or with *A. ovis*, or with *A. platys*.

In another aspect, the invention provides a method of malting a mammalian cell that is stably infected with an *Anaplasma* species such as *A. marginale, A. phagocytophilum, A. centrale, A. bovis, A. ovis*, and *A. platys*. Such a method includes contacting a mammalian adherent cell with the *Anaplasma* species to produce a mammalian cell stably infected with the *Anaplasma* species. For example, the adherent mammalian cell can be contacted with *A. marginale*, or with *A. phagocytophilum*, or with *A. centrale*, or with *A. bovis*, or with *A. ovis*, or with *A. platys*.

In an embodiment, the invention provides a method of making a mammalian cell that is stably infected with *Anaplasma marginale*. Such a method includes contacting a nucleated mammalian cell with *A. marginale* to produce a mammalian cell stably infected with *A. marginale*. In another embodiment, the invention provides a method of making a mammalian cell that is stably infected with *Anaplasma phagocytophilum*. Such a method includes contacting a mammalian adherent cell with *A. phagocytophilum* to produce a mammalian cell stably infected with *A. phagocytophilum*.

In still another aspect, the invention provides a method for propagating an *Anaplasma* species such as *A. marginale, A. centrale, A. bovis, A. ovis*, and *A. platys*. Such a method includes contacting a nucleated mammalian cell with the *Anaplasma* species to produce a mammalian cell stably infected with the *Anaplasma* species, and culturing the stably infected mammalian cell. For example, the nucleated mammalian cell can be contacted with *A. marginale*, or with *A. centrale*, or with *A. bovis*, or with *A. ovis*, or with *A. platys*. Generally, the cell is contacted with *A. marginale*. *A. marginale* can be obtained from tick cells (in vitro or in vivo) or red blood cells.

In still another aspect, the invention provides a method for propagating an *Anaplasma* species such as *A. marginale, A. phagocytophilum, A. centrale, A. bovis, A. ovis*, and *A. platys*. Such a method includes contacting a mammalian adherent cell with the *Anaplasma* species to produce a mammalian cell stably infected with the *Anaplasma* species, and culturing the stably infected mammalian cell. For example, the adherent mammalian cell can be contacted with *A. marginale*, or with *A. phagocytophilum*, or with *A. centrale*, or with *A. bovis*, or with *A. ovis*, or with *A. platys*. Generally, the cell is contacted with *A. phagocytophilum*. *A. phagocytophilum* can be obtained from HL-60 cells or white blood cells.

Generally, the mammalian cell is an endothelial cell or a Vero cell. Representative mammalian cells include, without limitation, a bovine corneal endothelial cell, a rhesus monkey microvascular endothelial cell, a human umbilical vascular endothelial cell, and a human microvascular endothelial cell. Typically, the *Anaplasma* species can be propagated in mammalian cells for at least 8 weeks (e.g., 10 weeks, 2 months, 6 months, 9 months, 12 months, 18 months, 2 years, 5 years, or 10 years).

In an embodiment, the invention provides a method for propagating *Anaplasma marginale*. Such a method includes contacting a nucleated mammalian cell with *A marginale* to produce a mammalian cell stably infected with *A. marginale*, and culturing the stably infected mammalian cell. In another embodiment, the invention provides a method for propagating *Anaplasma phagocytophilum*. Such a method includes contacting a mammalian adherent cell with *A. phagocytophilum* to produce a mammalian cell stably infected with *A. phagocytophilum*, and culturing the stably infected mammalian cell.

In another aspect, the invention provides a method for obtaining an *Anaplasma* species such as *A. marginale, A. centrale, A. bovis, A. ovis*, and *A. platys*. Such a method includes culturing a nucleated mammalian cell stably infected with the *Anaplasma* species, and isolating the *Anaplasma* species from the mammalian cell. For example, the nucleated mammalian cell can be infected with *A. marginale*, or with *A. centrale*, or with *A. bovis*, or with *A. ovis*, or with *A. platys*. Generally, the cell is infected with *A. marginale*. In an embodiment, the *Anaplasma* species is an attenuated *Anaplasma* species.

In another aspect, the invention provides a method for obtaining an *Anaplasma* species such as *A. marginale, A. phagocytophilum, A. centrale, A. bovis, A. ovis*, and *A. platys*. Such a method includes culturing a mammalian adherent cell stably infected with the *Anaplasma* species, and isolating the *Anaplasma* species from the mammalian cell. For example, the adherent mammalian cell can be infected with *A. marginale*, or with *A. phagocytophilum*, or with *A. centrale*, or with *A. bovis*, or with *A. ovis*, or with *A. platys*. Generally, the cell is infected with *A. phagocytophilum*. In an embodiment, the *Anaplasma* species is an attenuated *Anaplasma* species.

In one embodiment, the invention provides for a method for obtaining *Anaplasma* marginale. Such a method includes culturing a nucleated mammalian cell stably infected with *A. marginale*, and isolating *A. marginale* from the mammalian cell. In another embodiment, the invention provides a method for obtaining *Anaplasma phagocytophilum*. Such a method includes culturing a mammalian adherent cell stably infected with *A. phagocytophilum*, and isolating *A. phagocytophilum* from the mammalian cell.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides methods and materials related to propagating *Anaplasma* species in mammalian cells. Specifically, the invention provides for mammalian nucleated cells and mammalian adherent cells that are stably infected with an *Anaplasma* species, as well as methods and materials for malting such mammalian cells. In addition, the invention provides methods and materials for obtaining various *Anaplasma* species, e.g. *A. marginale* and *A. phagocytophilum*. The invention is based on the discovery that some mammalian cells can be stably infected with *Anaplasma* species making them useful as vehicles for propagating *Anaplasma* species in vitro.

Mammalian Host Cells Stably Infected with *Anaplasma* Species

The invention provides isolated mammalian cells that have been stably infected with *Anaplasma*. The term "isolated" as used herein with reference to a mammalian cell refers to a mammalian cell that has been separated from other cell types with which it is normally found in nature. Isolated mammalian cells include, without limitation, untransformed or transformed (e.g. immortalized) mammalian cells isolated from mammalian tissues. Other examples of isolated mammalian cells include, without limitation, hepatocytes isolated from liver and endothelial cells isolated from umbilical cord.

As used herein, the term "stably infected" refers to a host cell that (1) has been infected with an organism, i.e. an infective agent such as *A. marginale*, and (2) allows for multiplication of the infective agent within the host cell until the host cell lyses leading to release of infective agents from the host cell. When a culture of stably infected cells lyses, infective agents in the culture lysate can be passaged to a culture of uninfected cells. For example, a culture lysate containing infective agents can be used as an inoculum to infect other cells of the same or different cell line to generate a second culture of stably infected cells. In this way, an *Anaplasma* species can be propagated for at least 10 passages through a host cell line without loss of the infective agent. *Anaplasma* can be cultured in mammalian cells for weeks, months, or years. Loss of the infective agent can be monitored by examining inclusions observed in infected cells as described in Blouin et al. (1993) *Revue Elev Med vet Pays trop* 46:49-56 for bovine turbinate cells and bovine pulmonary aorta endothelial cells. Thus, a stably infected cell such as a stably infected Vero cell or endothelial cell can be used as a vehicle for propagating the *Anaplasma* species.

Mammalian host cells stably infected with an *Anaplasma* species include, without limitation, (1) mammalian nucleated cells that have been stably infected with *A. marginale*, and (2) mammalian adherent cells that have been stably infected with *A. phagocytophilum*. As used herein, an adherent cell refers to a cell that attaches firmly to a culture substrate (i.e., a plastic surface) in vitro. Adherent cells must be physically detached from the substrate (e.g., scraped off with a silicone rubber-coated blade or treated with an enzyme solution (e.g., trypsin). Examples of adherent cell types include endothelial cells, macrophages and other cells derived from the monocytic white blood cell lineage, fibroblasts, and epithelial cells. Adherent cells are generally derived from solid organs and white blood cells in the monocytic lineage (e.g., macrophages, histiocytes, and Kupffer cells). Non-adherent cells (e.g., red blood cells, HL-60 cells, or bone marrow cells other than those of the monocytic lineage) may settle loosely onto the substrate and can be resuspended by agitating the medium. Scraping or enzyme treatment is not required to resuspend non-adherent cells.

Endothelial cells are particularly useful hosts cells for achieving stable infection with *Anaplasma* species. Examples of useful host cells include bovine corneal endothelial cells (e.g., BCE C/D-1b cells; ATCC CRL-2048), rhesus monkey microvascular endothelial cells (e.g., RF/6A cells; ATCC CRL-1780), human umbilical vascular endothelial cells (HUV-EC-C; ATCC CRL-1730), human umbilical vein endothelial cells (HUVEC-12; ATCC CRL-2480), and African green monkey kidney cells (Vero cells; ATCC CCL-81). Examples of *Anaplasma* species include *A. marginale* and *A. phagocytophilum*. Other examples of *Anaplasma* species include, without limitation, *A. centrale, A. bovis, A. ovis*, and *A. platys*.

Mammalian host cells can be stably infected with *Anaplasma* species using methods known in the art. In one embodiment, *Anaplasma* can be added to the host cell culture, and the culture incubated under conditions typically used for culturing the particular host cell type. For example, a suitable amount (e.g. 1 mL) of a lysed cell suspension derived from a tick cell culture (e.g. ISE6 cells) in which 70% or more of the tick cells are stably infected with *A. phagocytophilum* can be added to a culture of the suitable mammalian host cell, e.g. an endothelial cell such as the RF/6A cell. The inoculated mammalian cell culture then can be grown under appropriate conditions, e.g., in L15B300 medium supplemented as described herein in tightly closed flasks incubated at 37° C. The resulting culture can be grown in this manner until cell lysis occurs. Before host cell lysis, *Anaplasma* can be observed as inclusion bodies in the cytoplasm of host cells. Once cell lysis occurs, the culture lysate can be used to inoculate uninfected cells as described above.

Detecting *Anaplasma*

*Anaplasma* can be detected by several methods including, without limitation, microscopic analysis of live cultures, as well as histochemical, immunocytological, and PCR analyses. Such methods are particularly useful for determining whether host cells such as mammalian endothelial cells have been stably infected with *Anaplasma.*

Histochemical analysis can be performed on infected cells stained with Giemsa stain. Infected cells then can be detected by observing the presence of *Anaplasma* inclusions in the cytoplasm, similar to those seen in vivo in neutrophilic granulocytes. Inclusions in heavily infected cells can completely fill the cytoplasm, and cause the cell to become distended. For example, a sample of endothelial cells infected with *A. marginale* and passaged for 9 months can be processed using the histochemical methods described herein. The presence of Giemsa-stained inclusions in the cytoplasms of endothelial cells indicates the presence of *A. marginale* in these cells.

Alternatively, *Anaplasma* can be detected by immunocytological methods with specific *A. marginale* or *A. phagocytophilum* antibodies that are fluorescently labeled. For example, a sample of endothelial cells infected with *A. phagocytophilum* and passaged for 6 months can be exposed to fluorescently labeled antibodies specific for *A. marginale* or *A. phagocytophilum*. The presence of *Anaplasma* in the cell sample is indicated by the presence of immunofluorescence after the cell sample has been washed with appropriate buffers to eliminate non-specific binding of the *Anaplasma* antibody.

*Anaplasma* also can be detected by PCR using oligonucleotide primers designed specifically to amplify only *Anaplasma* nucleic acid. PCR can be performed on nucleic acid isolated from *Anaplasma*-infected cells. Primers can be designed based upon nucleic acid sequences found in the *Anaplasma* genome. See, for example, The Ehrlichia Research Laboratory, Ohio State University Health Sciences Center, College of Veterinary Medicine, Columbus, Ohio, and Animal Disease Research Unit-USDA-ARS, Dept. of Veterinary Microbiology and Pathology and the College of Veterinary Medicine, Washington State University, Pullman, Wash.). Primers that amplify an *Anaplasma* nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence specificity and to initiate synthesis but not so long that fidelity is reduced during oligonucleotide synthesis). Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length).

Use of Mammalian Cells Stably Infected with *Anaplasma*

Mammalian host cells stably infected with an *Anaplasma* species can be used for a variety of purposes including propagation of selected *Anaplasma* species. For example, mammalian host cells such as RF/6A cells that are stably infected with *A. phagocytophilum* can be a source of infectious *A. phagocytophilum* since the infected RF/6A cells allow for the intracellular multiplication of infectious *A. phagocytophilum*. Subsequent host cell lysis results in release of infectious *A. phagocytophilum* into the culture medium. The resulting culture lysate can be used as an inoculum for infecting uninfected cells. Using such procedures and passaging through numerous cell cultures, *A. phagocytophilum* can be propagated in vitro for four months or longer.

Infectious *A. phagocytophilum* propagated in this manner can be used to infect other host cell types for pathogenesis studies. Stably infected host cells can be cultured for various lengths of time before cell lysis necessitates passage to an uninfected cell or cell culture. The length of time between passages can vary depending on the particular culture conditions, host cell type, and *Anaplasma* species, and can be from less than one week to about one month or more. The length of time between passages for *A. phagocytophilum* grown in RF/6A cells under conditions described herein, for example, is one week or less.

Mammalian host cells stably infected with an *Anaplasma* species also can be used to develop materials for the treatment of anaplasmosis and anaplasmosis-related diseases, e.g., ehrlichioses such as human granulocytic ehrlichiosis (HGE), and determining the efficacy of such anaplasmosis treatment materials. For example, mammalian host cells stably infected with an *Anaplasma* species can be used as a source of *Anaplasma*. *Anaplasma* isolated from host cell cultures using methods described herein can be used for developing anaplasmosis treatment materials such as agents for treating, controlling, or preventing anaplasmosis (e.g., *Anaplasma* vaccines), as well as growth promoters, feed additives, pharmaceuticals, nutraceuticals, antibiotics, and antimicrobial agents. Anaplasmosis treatment material formulations can include vaccine formulations containing whole microorganisms or antigen preparations containing portions of the whole microorganism. The use of whole microorganisms in a treatment material formulation typically involves attenuation. The term "attenuated" as used herein refers to a reduction in the virulence of an infective agent such as *A. marginale* or *A. phagocytophilum*. Attenuation can be performed using various methods including, without limitation, exposure to heat (e.g., heat-killing), and chemical inactivation (e.g., treatment with β-propiolactone). Alternatively, an infective agent such as an *Anaplasma* species can be cultivated in vitro until the organism has lost the ability to infect host animals or humans. Treatment material formulations containing attenuated organisms can be prepared in accordance with methods standard in the art.

Attenuated whole *Anaplasma* organisms and/or *Anaplasma* antigen preparations containing portions of whole *Anaplasma* can be combined with physiologically acceptable carriers. Such physiologically acceptable carriers include, without limitation, buffered salt solutions, phosphate buffered saline, and cell culture medium. In addition, treatment material formulations also can include adjuvants, such as alum, ISCOMs, complete Freund's adjuvant, incomplete Freund's adjuvant, and saponin.

Anaplasmosis treatment materials can be administered by a variety of routes including, without limitation, intravenous, intraperitoneal, intramuscular, subcutaneous, intrathecal, and intradermal injection, by oral administration, by inhalation, or by gradual perfusion over time. For example, a solution preparation containing heat-killed *Anaplasma* can be given to a host by intramuscular injection. It is noted that the duration of treatment with any of the materials described herein can be any length of time from as short as one day to as long as a lifetime (e.g., many years). For example, an anaplasmosis treatment material can be administered once a year over a period of ten years. It is also noted that the frequency of treatment can be variable. For example, an anaplasmosis treatment material can be administered once daily for 20 days, then twice monthly for 6 months, and then once yearly indefinitely. Typically, an anaplasmosis treatment material is administered at a frequency that induces and maintains a protective effect (i.e., a protective immune response to infection by an *Anaplasma* species) in the treated mammal. Treatment materials also can ameliorate and/or prevent the development of symptoms associated with anaplasmosis (e.g., anemia, weakness, and retarded growth).

Any method can be used to determine if a particular immune response is induced. For example, antibody responses against particular antigens can be determined using immunological assays (e.g., ELISA) such as those described herein. In addition, clinical methods that can assess the severity of a particular disease state (e.g., *Anaplasma* infection) can be used to determine if a desired immune response is induced.

Antigen preparations are also useful for diagnostic assays, such as ELISA, solid phase immunoassays, complement fixation tests, delayed-type hypersensitivity response assays and the like. To obtain an *Anaplasma* species likely to include antigens that react with antibodies produced after mammalian infection, antigens can be prepared from *Anaplasma* species obtained from stably infected mammalian endothelial cells.

*Anaplasma* organisms can be used to determine the efficacy of an anaplasmosis treatment material. Once given a particular anaplasmosis treatment material, a mammal can be challenged with *Anaplasma* organisms. Once challenged, the mammal is assessed to determine the presence or absence of an *Anaplasma* infection. For example, a cow given an *Anaplasma* vaccine can be challenged with *A. marginale* and then assessed to determine the presence or absence of an *Anaplasma* infection. Determining the presence or absence of an *Anaplasma* infection in a treated mammal provides an indication of the efficacy of that treatment material. For example, if a cow treated with an *Anaplasma* vaccine develops an *Anaplasma* infection after being challenged with *A. marginale*, then that *Anaplasma* vaccine may not be effective in protecting that cow against *Anaplasma* infection. Alternatively, if a cow treated with an *Anaplasma* vaccine does not develop an *Anaplasma* infection after being challenged with *Anaplasma*, then that *Anaplasma* vaccine likely is effective in protecting that cow against *Anaplasma* infection.

The invention will be further described in the following examples, which do not limit the scope of the invention described in the claims.

EXAMPLES

Example 1

Host Cell Lines

Tick cell line ISE6, from embryos of the black-legged tick, *Ixodes scapularis*, was used for propagation of both *A. marginale* and *A. phagocytophilum* (Munderloh et al., 1996, *J. Med. Entomol.,* 33:656-64; Munderloh et al., 1996, *J. Clin. Microbiol.,* 34:664-670; and Munderloh et al., 1999, *J. Clin. Microbiol.,* 37:2518-2524). Uninfected cells were grown in L15B300 with 5% tryptose phosphate broth (Difco Laboratories, Detroit, Mich., USA), 5% heat-inactivated fetal bovine serum (FBS, Harlan, Indianapolis, Ind., USA), and 0.1% bovine lipoprotein concentrate (ICN, Irvine, Calif., USA), pH 7.2. Medium for infected cultures was additionally supplemented with 25 mM HEPES [N-(2-Hydroxyethyl)piperazine-N'-(2-ethanesulfonic acid)] and 0.25% $NaHCO_3$, and the pH was adjusted to 7.5-7.7. All cultures were maintained at 34° C. *Anaplasma* were passaged by transferring 1/50th of an infected cell suspension to a new flask of tick cells every 2 weeks.

The mammalian cells employed in this study were endothelial lines RF/6A (American Type Culture Collection, Mansssas, Va., USA; ATCC CRL-1780) from the retina choroid of a normal fetal rhesus (*Macaca mulatta*), BCE C/D1-b, an adult bovine corneal endothelial cell line that is free of bovine viral diarrhea/mucosal disease virus (ATCC CRL-2048), the human microvascular cell line HMEC-1 (Ades et al., 1992, *J. Invest. Dermatol.*, 99:683-690), and primary human skin microvascular endothelial cells (MVEC; VEC Technologies, Inc. Rensselaer, N.Y., USA). The human promyelocytic leukemia cell line HL-60 (ATCC CCL-240) was used to propagate *A. phagocytophilum* as described earlier (Goodman et al., 1996, *N. Engl. J. Med.*, 334:209-215). Rhesus and bovine endothelial cells were grown in closed flasks in L15B300 supplemented as for infected ISE6 cells, except that 10% FBS and 50 mM HEPES was used. HL-60 cells were maintained in RPMI1640 (Bio Whittaker, Walkersville, Md., USA); HMEC-1 cells were grown in MCDB 131 (Mediatech, Herndon, Va., USA) with 0.5 µg/ml cortisone; and MVEC were propgated in complete MCDB-131 from VEC Technologies, all with 10% FBS (HyClone, Logan, Utah, USA) and in a 5% $CO_2$ atmosphere. Mammalian cell cultures were kept at 37° C. Endothelial cells were detached using trypsin (Gibco, Grand Island, N.Y., USA), and diluted 4-fold once a week for subculturing.

Example 2

Infection of Endothelial Cells with *A. marginale* and *A. phagocytophilum*

For *A. marginale*, the Virginia isolate Am291 in its 36th passage in ISE6 cells was used as the primary inoculum. For *A. phagocytophilum*, ISE6 cells infected with the 24th passage of the isolate HGE2 was used. Initially, 0.5 ml of an *Anaplasma* culture in which 80% or more of the tick cells were infected and releasing bacteria due to cell lysis, was added to a 25 $cm^2$ flask with a confluent endothelial cell layer, lines RF/6A, BCE C/D-1b, and HMEC-1, or primary MVEC. For some experiments with HGE2, endothelial cells were alternatively inoculated with 50 µl (equivalent to $5\times10^3$ infected cells) of *A. phagocytophilum* from HL-60 cells at various passage levels of 23 and higher. The organisms were harvested from infected HL-60 cells by mechanical rupture as a host cell-free suspension as described, and added directly to recipient cultures in 5 ml medium per 25 $cm^2$ flask, or 0.5 ml medium per well of a 24-well plate. Cultures were incubated in their respective media and atmospheric conditions at 37° C. Cultures were monitored daily by phase contrast microscopy. For continuous passage in endothelial cells, infected cell layers were scraped off the growth surface, the suspension repeatedly pipetted to disrupt cell clumps, and a portion transferred to a fresh, confluent cell layer.

Example 3

Light Microscopy

For Giemsa-staining or immunofluorescence assays (IFA), 25 cm2 cell layers were rinsed once with phosphate buffered saline, pH 7.5 without $Ca^{2+}$ and $Mg^{2+}$ (PBS), and detached from the substrate by trypsinization. Cells were resuspended in growth medium, and $10^4$ cell aliquots spun onto microscope slides using a Cytospin (Shandon Southern Instruments, Sewickley, Pa., USA) centrifuge at 60×g for 5 min. Slides were fixed in absolute methanol for 5 min, air-dried briefly, and immersed in a buffered (pH 6.8) solution of 4% Giemsa's stain (Karyomax, Gibco, Grand Island, N.Y., USA) for 30 min at 37° C.

For IFA, fixed, air dried cell spots were overlaid with primary antibody diluted as outlined below, and incubated in a humid atmosphere at room temperature for 1 hr. Slides were rinsed in PBS, and immersed in PBS with 10% bovine serum albumin (BSA; Serologicals Corporation, Norcross, Ga., USA) for 10 min. They were then dipped in distilled water, rinsed in PBS, and the cells covered with fluorescein isothiocyanate (FITC)-labeled IgG of the appropriate species specificity for 1 hr at room temperature in a humid chamber. Finally, the slides were rinsed with PBS, counterstained in Evans' Blue (0.005% in PBS) and covered with antifade mounting medium (Vector Laboratories, Burlingame, Calif., USA).

Primary antisera used were a bovine hyperimmune serum to *A. marginale* initial bodies harvested from erythrocytes (kindly provided by Dr. Katherine M. Kocan, Oklahoma State University, Stillwater; Munderloh et al., 1996, *J. Med. Eutonol.*, 33:656-64), and a mouse monoclonal antibody against MSP2 of *A. phagocytophilum* (a generous gift from Dr. Russell C. Johnson, University of Minnesota; Ravyn et al., 1999, *Am. J. Trop. Med. Hyg.*, 61:171-176). Bovine anti-*A. marginale* serum was diluted 1:200, and the monoclonal antibody was diluted 1:10,000.

Slides were viewed and photographed under oil immersion at 100× magnification using a Nikon Eclipse E400 microscope, fitted for epifluorescence and equipped with a Nikon DXM1200 digital camera.

Example 4

Electron Microscopy

Cultures estimated by phase contrast microscopy to be 50% or more infected, were scraped off their substrate, approximately $5\times10^4$ cells were pipetted into 1 ml of Ito's modified fixative (Kurtti et al., 1994, *Can. J. Zool.*, 72:977-994), and incubated on ice for 1 hr. Fixed cells were collected by centrifugation at 275×g for 5 min, and resuspended in 1.5 ml fresh fixative. Cell pellets were postfixed in osmium tetroxide and dehydrated in graded changes of an ascending alcohol series. The pellet was embedded in Spurr's epoxy resin and thin sections were stained with methanolic uranyl acetate and Reynold's lead citrate.

Example 5

Polymerase Chain Reaction (PCR)

Table 1 lists the primers used in this study. To verify the identity of *A. marginale* or *A. phagocytophilum* from endothelial cell culture, four sets of primers were employed; one directed at the 16S rDNA of the genera *Ehrlichia* and *Anaplasma* (PER1, PER2), yielding a 451 bp product (Goodman et al., 1996, *N. Engl. J. Med.*, 334:209-215), two that bind to the msp2 (p44) gene of *A. phagocytophilum* (p44-1, p44-2; and p3708, p4257) resulting in a 1,279 bp and a 541 bp product, respectively (Ijdo et al., 1998, *Infect. Immun.*, 66:3264-3269; Zhi et al., 1999, *J. Biol. Chem.*, 274:17828-17836), and one that is specific for the conserved region of the *A. marginale* msp1β gene (AL34S, BAP-2; Barbet and Allred, 1991, *Infect. Immun.*, 59:971-976; Stich et al., 1993, *J. Med. Entomol.*, 30:789-794) and mediates amplification of a 407 bp target. In control reactions, sterile water was substituted for DNA. Endothelial cell-culture derived *Anaplasma* were separated from host cells, solubilized in lysis buffer, and DNA extracted using the PureGene kit (Gentra Systems, Minneapolis, Minn., USA) as described (Goodman et al., 1999, *J. Clin. Invest.*, 103:407-412). DNA was dissolved in sterile water (500 μl for each DNA pellet harvested from one 25 cm² culture), and stored at −20° C. Two μl of DNA was used in each 50 μl reaction mixture containing 20 mM Tris-HCl, pH 8.4, 50 mM KCl, 2.5 mM $MgCl_2$, 200 μM each of deoxynucleotides, 0.5 μM of each oligonucleotide primer, and 1.25 units of Taq DNA polymerase (Promega, Madison, Wis.). DNA was initially denatured for 3 min at 95° C., and then amplified in a Robocycler (Stratagene, La Jolla, Calif., USA) during 40 cycles consisting of a denaturation step of 30 sec at 94° C., annealing for 30 sec at 45° C., and elongation for 45 sec at 72° C., with a final elongation step of 5 min. DNA extracted from tick cells cultures (for *A. marginale*, Munderloh et al., 1996 *J. Med. Entomol.*, 33:656-64) or HL-60 cell cultures (for *A. phagocytophilum*, Goodman et al., 1996, *N. Engl. J. Med.*, 334:209-215) was used as a positive control, and reactions mixtures containing water instead of DNA served as negative controls. PCR products were separated by electrophoresis through 1% agarose gels in 0.5× Tris-Borate-EDTA buffer, and visualized by ethidium bromide staining and ultraviolet transillumination.

All primer pairs resulted in amplification of the correct size product of only their target DNA.

every 10 days. *A. marginale* grew more slowly in RF/6A than *A. phagocytophilum*. The initial passage from tick cells caused infection in 100% of cells in 10 days, but subsequent subcultures were made with a 10-fold dilution of infected cells every 2 weeks. These growth rates in RF/6A cells have remained stable for *A. marginale* and *A. phagocytophilum*.

Infection dynamics of both *Anaplasma* spp. in BCE C/D-1b bovine endothelial cells were different from those in rhesus cells. The initial transfer of *A. marginale* from ISE6 tick cells resulted in 70% infection within 30 days, when the cells were further passaged to fresh BCE C/D-1b at a 1:5 dilution. The next 1:5 passage was carried out with 90% infected cells 28 days later, but this culture failed to become established, and was subsequently discarded. Similarly, *A. phagocytophilum* could be transferred three times in BCE C/D-1b cells within a time-span of 46 days, growing to infect 80-90% of the cells each time, and then stopped replicating further, and was also discontinued. When BCE C/D-1b cells were inoculated with *Anaplasma* derived from RF/6A cells, they behaved like those derived from tick cells, and the bacteria stopped growing after 3 or 4 transfers. These cultures were not pursued further. In RF/6A and BCE C/D-1b, control of the medium pH at or above 7.5 was critical, and was achieved by doubling the concentration of HEPES over that used in tick cells.

Only *A. phagocytophilum* replicated in HMEC-1 and MVEC cells. Bacteria taken from either HL-60 or RF/6A cultures readily invaded and multiplied in HMEC-1, while

TABLE 1

Oligonucleotides

| Primer Designation, Specificity and Target | | Nucleotide Sequence (5' → 3') (SEQ ID NO:) | Reference |
|---|---|---|---|
| p44-1 | *Anaplasma phagocytophilum* | AGC GTA ATG ATG TCT ATG GC (1) | a |
| p44-2 | p44 (insp2) | ACC TAA CAC CAA ATT CCC (2) | a |
| p3708 | *Anaplasma phagocytophilum* | GCT AAG GAG TTA GCT TAT GAT (3) | b |
| p4257 | p44 (msp2) | AAG AAG ATC ATA ACA AGC ATT (4) | b |
| PER1 | *Anaplasma* and *Ehrlichia*-wide | TTT ATC GCT ATT AGA TGA GCC TAT G (5) | c |
| PER2 | 16S rDNA | CTC TAC ACT AGG AAT TCC GCT AT (6) | c |
| BAP-2 | *Anaplasma marginale* | GTA TGG CAC GTA GTC TTG GGA TCA (7) | d |
| AL34S | msp1β | CAG CAG CAG CAA GAC CTT CA (8) | e | a Ijdo et al., 1998, Infect. Immun., 66:3264-9;
b Zhi et al., 1999, J. Biol. Chem., 274:17828-36;
c Goodman et al., 1996, N. Eng. J. Med., 334:209-15;
d Barbet and Allred, 1991, Infect. Immun., 59:971-6;
e Stich et al., 1993, J. Med. Entomol., 30:789-94.

Example 6

Growth of *Anaplasma* in Endothelial Cell Lines

Both *A. marginale* and *A. phagoytophilum* that had been continuously propagated in *I. scapularis* cell line ISE6, when inoculated onto RF/6A rhesus, BCE C/D-1b bovine or HMEC-1 human endothelial cell layers, invaded these cells and replicated inside intracellular inclusions. After the initial inoculation with infected tick cells, inclusions of either *Anaplasma* sp. could be detected by phase contrast microscopy in RF/6A cells within several days. The first passage of *A. phagocytophilum* from ISE6 cells caused RF/6A lysis within 2 weeks, but subsequent replication was much faster, and by the 10th passage, cultures were routinely subcultured by diluting 100- or 200-fold every 5-7 days, or 1,000-fold

*A. marginale* transferred at the same time from RF/6A cells did not. ISE6 culture-grown *A. phagocytophilum* also infected HMEC-1 cells, but took 10 or more days to become apparent by light microscopy. Once established, it could then be passaged at the same schedule as bacteria transferred from HL-60 cells to HMEC-1.

Example 7

Light Microscopic Features of *Anaplasma* in Endothelial Cells

The appearance of *A. marginale* and *A. phagocytophilum* was distinct at the light microscopic level. Notably, *A. marginale* formed large inclusions in RF/6A that appeared smooth and solid by phase contrast microscopy during the first few days. Individual bacteria, too tightly juxtaposed to each other to discern at first, subsequently condensed and became discrete, visible as a large number of tiny granules contained within a single inclusion. Eventually, the host cell ruptured and released bacteria that spread through the culture, causing complete destruction of infected monolayers. By contrast, *A. phagocytophilum* tended to form numerous smaller and very distinct inclusions (morulae) in each cell in which individual *Anaplasmas* were always distinguishable. RF/6A cells were infected with *A. marginale* or *A. phagocytophilum*, and HMEC-1 and MVEC cells were infected with *A. phagocytophilum*. *A. marginale* inclusions diffuse were, and large morulae were released from a ruptured host cells. Many well-defined morulae were evident in *A. phagocytophilum*-infected cells, with greater numbers accommodated in the larger RF/6A host cell.

Both the bovine anti-*A. marginale* and the anti-*A. phagocytophilum* antibodies reacted with their target antigen in a specific manner. Either antibody preparation preferentially stained the periphery of individual bacteria or small groups of bacteria in a morula, resulting in a honeycombed or fish net-like pattern that was most noticeable in RF/6A and BCE C/D-1b cells, and less so in HMEC-1 and MVEC. In the larger RF/6A and BCE C/D-1b cells, the *Anaplasma* inclusions were less compact than in HMEC-1 and MVEC cells, in which *A. phagocytophilum* formed primarily well defined and dense, rounded morulae.

Example 8

Electron Microscopy

Ultrastructural images confirmed many of the light microscopic observations. *A. marginale* formed few but large inclusions per cell. These often contained bacteria that differed in degree of condensation and in shape. Many appeared to progress from being tightly packed with reticulate forms that abutted and conformed to each other like pieces of a mosaic, to being loosely filled with condensed bacteria. A single endosome had regions in which reticulated forms were grouped closely together, with dense forms loosely filling the remainder of the inclusion. By contrast, *A. phagocytophilum* morulae were small and numerous, and most contained individual organisms of the same morphologic type, i.e., either reticulated, or dense forms. Rarely, *A. phagocytophilum* morulae harbored both dense and reticulate bacteria. The most unusual-looking bacteria were found in *A. phagocytophilum*. Sometimes rod-shaped, sometimes more rounded, they were electron dense and showed evidence of extensive invaginations and infolding of membranes. Reticulate forms present in the same morula indicate these are not artifacts.

Example 9

Preparation of Cell Lysates Containing *Anaplasma* Antigens

*Anaplasma* antigens produced from Vero or endothelial cell cultures are recognized by sera from infected animals and humans, and are useful for serologic diagnosis. Vero or endothelial cell cultures, infected and maintained as described in Example 1, were cultured until 90% or more of the cells were infected with either *A. marginale* or *A. phagocytophilum*. The infected cells were scraped from the flask bottom and then sheared by repeated passage through a 27-gauge needle. Alternatively, the cells were disrupted by sonication. The sheared cells were then centrifuged at 400×g to settle large debris. The supernatant, containing *Anaplasma*, was concentrated by centrifugation at 2000×g for 20 minutes. The resulting pellet, containing *Anaplasma*, was then further purified by passage through a 30% renografin density gradient. Purified *Anaplasma*, collected at the bottom of the gradient were resuspended in PBS, and then lysed by sonication. The protein concentration in the lysate was determined using standard techniques, and then adjusted to 5 µg/mL using 0.015 M $Na_2CO_3$ in 0.035 M $NaHCO_3$, pH 9.6.

Example 10

Detection of *Anaplasma* Antigens in Cell Lysates

To detect *Anaplasma* antigens in cell lysate preparations, 100 µL aliquots of the diluted lysate prepared as described above were added to each well of a 96-well, amine-binding microtiter plate. After 24 hours at 4° C., the plates were washed three times with PBS, pH 7.2, and blocked with PBS containing 0.05% Tween 20 and 1% bovine serum albumin (BSA). After 1 hour at room temperature, the plates were washed three times with PBS, and 100 µL of sera serially diluted 10-fold in PBS were added to the wells. After one hour at room temperature, unbound sera were removed with three PBS washes, and then horseradish peroxidase-labeled antibodies recognizing IgG of the appropriate species were added to the wells. After one hour at room temperature unbound antibodies were removed with three PBS washes, and the bound antibodies in the wells were treated with 0.4 mg/mL o-phenylenediamine phosphate for 30 min. The reaction was stopped by addition of 1N $H_2SO_4$, and absorbance at 490 nm was read using a plate reader or spectrophotometer. The absorbance values of test sera were compared with those from known negative sera. Test sera were considered positive when their absorbance values exceeded a value that corresponded to 3 standard deviations above the mean absorbance value for negative sera. A positive value is typically above 0.500. Using this method, *Anaplasma* antigens were detected in lysates prepared from Vero and RF/6A cells infected with *A. marginale*. Therefore, *Anaplasma* antigens can be prepared from Vero or endothelial cell cultures.

Example 11

Detection of *Anaplasma* Antigens in Whole Cells

To detect *Anaplasma* antigens within confines of a mammalian host cell, Vero or endothelial cell cultures, infected and maintained as described above were cultured until 70% or more of the cells were infected with either *A. marginale* or *A. phagocytophilum*. The growth medium was then removed from a flask and the cell layer was rinsed once with phosphate buffered saline (PBS), pH 8. The rinsed cell layer was then flooded with 3 mL 0.25% trypsin in PBS at pH 8. After one minute at room temperature, the trypsin solution was removed, and the culture was incubated at 37° C. until cells became rounded and detached from the growth substrate. The detached cells were suspended in about 5 mL of growth medium, and about 5 µL of the cell suspension was deposited into wells of 18-well slides. The cells were allowed to air dry over night, and were then immersed in 100% methanol or a mixture of 50% methanol and 50% acetone. After 10 minutes, the slides were briefly dried at room temperature, and stored desiccated at −20° C. To detect the presence of specific antibodies in patient sera, wells were sequentially incubated with serial dilutions of patient serum in PBS. After 60 minutes at 37° C., the slides were rinsed three times in PBS. Labeled secondary antibodies of the appropriate specificity (either anti-bovine or anti-human IgG) were then added to the wells. After 60 minutes at 37° C., the slides were again rinsed three times in PBS. The rinsed slides were mounted to coverslips using antifade mounting medium (e.g., PBS, 1% BSA (bovine serum albumin), 10% (w/v) triethylenediamine, and 10% glycerol, or Vectashield from Vector Laboratories), and viewed under UV illumination at 100× magnification using a microscope fitted for epifluorescence and a filter cube appropriate for the fluorescent label (either FITC or Rhodamine). In this way, *Anaplasma* antigens were detected in Vero, BCE C/D 1-b and RF/6A cells by their bright green or red fluorescence against the non-fluorescent background of the host cell.

Example 12

Vaccine Compositions Including *Anaplasma* Organisms Obtained from Mammalian Cells Vero or endothelial cells infected with *A. marginale* or *A. phagocytophilum* are cultured until phase contrast microscopy and/or cell samples stained with Giemsa stain indicate that a majority (e.g., 90% or more) of the cells are infected. Cultures are harvested, and *Anaplasma* microorganisms are purified through density gradient centrifugation as described in Example 2. Purified *Anaplasma* microorganisms are counted using a Petroff Hausser bacteria counter, and resuspended in PBS at a density of approximately $5\times10^9$ microorganisms/mL. *Anaplasma* microorganisms are inactivated with β-propiolactone as described by Kocan et al. (2001, *Vet. Parasitol.*, 102(1-2): 151-61).

*Anaplasma* microorganisms ($2\text{-}5\times10^{10}$ per dose) are mixed with adjuvant. The microorganisms are either absorbed onto aluminum hydroxide (alum) or emulsified with an oil-based adjuvant such as Adjuvant XtendIII (Novartis, Larchwood, Iowa). The microorganism/adjuvant mixture is administered to a mammal over a specified period (e.g., two times subcutaneously at four-week intervals, and once per year thereafter). The exact adjuvant and immunization protocol will vary depending on the species immunized and the treatment outcome desired.

These protocols provide improved vaccine compositions based on *A. marginale* or *A. phagocytophilum* antigens prepared from mammalian cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated mammalian cell stably infected with *Anaplasma marginale*, wherein said mammalian cell is a nucleated monkey cell.

2. The isolated mammalian cell of claim 1, wherein said mammalian monkey cell is an endothelial cell.

3. The isolated mammalian cell of claim 2, wherein said cell is a rhesus monkey microvascular endothelial cell.

4. A method of making a mammalian cell that is stably infected with *Anaplasma marginale*, said method comprising contacting a nucleated mammalian monkey cell with said *A. marginale* to produce a mammalian cell stably infected with said *A. marginale*.

5. A method for propagating *Anaplasma marginale*, said method comprising contacting a nucleated mammalian monkey cell with said *A. marginale* to produce a mammalian monkey cell stably infected with said *A. marginale* and culturing said stably infected mammalian monkey cell.

6. The method of claim 5, wherein said *A. marginale* is obtained from tick cells or red blood cells.

7. The method of claim 5, wherein said mammalian monkey cell is an endothelial cell or a Vero cell.

8. The method of claim 7, wherein said mammalian cell is a rhesus monkey microvascular endothelial cell.

9. The method of claim 5, wherein said *A. marginale* is propagated for at least 8 weeks.

10. A method for obtaining *Anaplasma marginale*, said method comprising culturing a nucleated mammalian monkey cell stably infected with said *A. marginale*, and isolating said *A. marginale* from said mammalian monkey cell.

11. The method of claim 10, wherein said *A. marginale* is cultured under conditions in which said *A. marginale* is attenuated.

* * * * *

UNITED STATES PATENT AND TRADEMARK OFFICE
CERTIFICATE OF CORRECTION

PATENT NO. : 7,361,504 B2  
APPLICATION NO. : 10/524338  
DATED : April 22, 2008  
INVENTOR(S) : Ulrike G. Munderloh Page 1 of 1

It is certified that error appears in the above-identified patent and that said Letters Patent is hereby corrected as shown below:

Title Page, item [56] References Cited, Other Publications, Mutunga et al. reference, please delete "*ruminanrium*" and insert --*ruminantium*-- therefor;

Column 1, line 4, please insert

--STATEMENT AS TO FEDERALLY FUNDED RESEARCH

This invention was made with government support under National Institutes of Health grant #AI42792. The government has certain rights in the invention.--;

Column 18, line 61 (Claim 5), after "marginale" please insert --,--.

Signed and Sealed this

Twenty-sixth Day of August, 2008

JON W. DUDAS  
*Director of the United States Patent and Trademark Office*

```
                         SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
agcgtaatga tgtctatggc                                              20

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
acctaacacc aaattccc                                                18

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide

<400> SEQUENCE: 3
```

```
gctaaggagt tagcttatga t                                              21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide

<400> SEQUENCE: 4
aagaagatca taacaagcat t                                              21

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide

<400> SEQUENCE: 5
tttatcgcta ttagatgagc ctatg                                          25

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide

<400> SEQUENCE: 6
ctctacacta ggaattccgc tat                                            23

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide

<400> SEQUENCE: 7
gtatggcacg tagtcttggg atca                                           24

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
cagcagcagc aagaccttca                                                20
```